(12) United States Patent
Jansheski et al.

(10) Patent No.: US 7,954,496 B2
(45) Date of Patent: *Jun. 7, 2011

(54) DENTAL GUARD

(75) Inventors: John M. Jansheski, Maryville, TN (US); Ronald W. Spencer, Maryville, TN (US)

(73) Assignee: Dentek Oral Care, Inc., Maryville, TN (US)

( * ) Notice: Subject to any disclaimer, the term of this patent is extended or adjusted under 35 U.S.C. 154(b) by 0 days.

This patent is subject to a terminal disclaimer.

(21) Appl. No.: 11/672,683

(22) Filed: Feb. 8, 2007

(65) Prior Publication Data

US 2008/0138755 A1 Jun. 12, 2008

Related U.S. Application Data

(63) Continuation-in-part of application No. 11/608,274, filed on Dec. 8, 2006.

(51) Int. Cl.
*A61C 5/14* (2006.01)
*A61C 3/00* (2006.01)
*A61F 5/56* (2006.01)

(52) U.S. Cl. ............................. 128/859; 128/848; 433/6
(58) Field of Classification Search .......... 128/859–862, 128/848; 433/6–7
See application file for complete search history.

(56) References Cited

U.S. PATENT DOCUMENTS

| | | | |
|---|---|---|---|
| 3,532,091 A * | 10/1970 | Lerman ......................... | 128/861 |
| 4,114,614 A * | 9/1978 | Kesling ......................... | 128/861 |
| 4,862,903 A | 9/1989 | Campbell | |
| 5,234,005 A | 8/1993 | Kittelsen et al. | |
| 5,259,762 A | 11/1993 | Farrell | |
| 5,277,202 A | 1/1994 | Hays | |
| 5,277,203 A | 1/1994 | Hays | |
| 5,339,832 A | 8/1994 | Kittelsen et al. | |
| 5,447,168 A | 9/1995 | Bancroft | |
| 5,462,066 A | 10/1995 | Snyder | |
| 5,566,684 A | 10/1996 | Wagner | |
| 5,624,257 A * | 4/1997 | Farrell ......................... | 433/6 |
| 5,636,379 A | 6/1997 | Williams | |
| 5,682,904 A | 11/1997 | Stinnett | |
| 5,732,715 A | 3/1998 | Jacobs et al. | |
| 5,746,221 A | 5/1998 | Jones et al. | |
| 5,829,441 A | 11/1998 | Kidd et al. | |
| 5,921,240 A | 7/1999 | Gall | |

(Continued)

*Primary Examiner* — Patricia M Bianco
*Assistant Examiner* — Ophelia Hawthorne
(74) *Attorney, Agent, or Firm* — Luedeka, Neely & Graham, P.C.

(57) ABSTRACT

A custom-fitted dental appliance prevents grinding contact between upper and lower teeth of a wearer. The appliance includes a base member having a generally U-shaped horizontal portion with opposing posterior sections and an anterior section disposed between the posterior sections. The anterior section has an arcuate curvature substantially matching the curvature of the dental arch of most wearers. The base member has a vertical portion connected to a forward edge of the horizontal portion. The vertical portion of the base member has an arcuate curvature substantially following the curvature of the anterior section. The appliance includes over-molded anterior occlusal pads and molar pads that are attached to the upper surfaces of the base member. An over-molded anterior flange is attached to the vertical portion of the base member. The anterior occlusal pads, molar pads and anterior flange are formed from a thermoplastic material having a Vicat softening temperature below that of the base member. After heating the appliance to above the softening temperature of the over-molded portions, the anterior occlusal pads, molar pads and anterior flange may be custom fitted to the upper teeth and gums of the wearer.

18 Claims, 5 Drawing Sheets

U.S. PATENT DOCUMENTS

| | | |
|---|---|---|
| 6,003,515 A | 12/1999 | Maness |
| 6,053,168 A | 4/2000 | Sue |
| 6,371,758 B1 * | 4/2002 | Kittelsen ............... 433/6 |
| 6,581,604 B2 | 6/2003 | Cook |
| 6,637,436 B2 | 10/2003 | Farrell |
| 6,691,710 B2 | 2/2004 | Kittelsen et al. |
| 6,820,623 B2 | 11/2004 | Cook |
| 6,830,051 B1 | 12/2004 | Lesniak et al. |
| 6,932,088 B1 | 8/2005 | Berghash |
| 6,935,857 B1 | 8/2005 | Farrell |
| 6,986,354 B1 * | 1/2006 | Burns ................. 128/859 |
| 7,128,072 B2 * | 10/2006 | Bancroft ............... 128/859 |
| 7,210,483 B1 * | 5/2007 | Lesniak et al. ........... 128/861 |
| 2003/0111108 A1 | 6/2003 | Bancroft |
| 2004/0154626 A1 | 8/2004 | Washburn et al. |
| 2005/0034733 A1 | 2/2005 | Liddle et al. |
| 2005/0115571 A1 | 6/2005 | Jacobs |
| 2005/0247318 A1 | 11/2005 | Mohindra |
| 2005/0284489 A1 | 12/2005 | Ambis, Jr. |
| 2006/0065277 A1 | 3/2006 | Jacobs |
| 2006/0107963 A1 | 5/2006 | Ibsen et al. |
| 2006/0130851 A1 | 6/2006 | Mathias |
| 2006/0207610 A1 | 9/2006 | Anonsen |

* cited by examiner

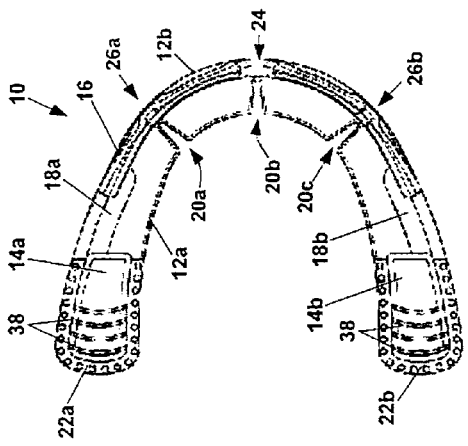
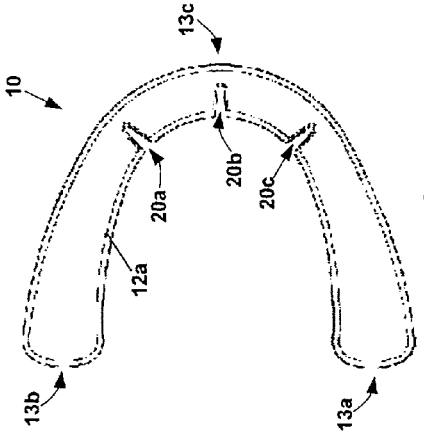
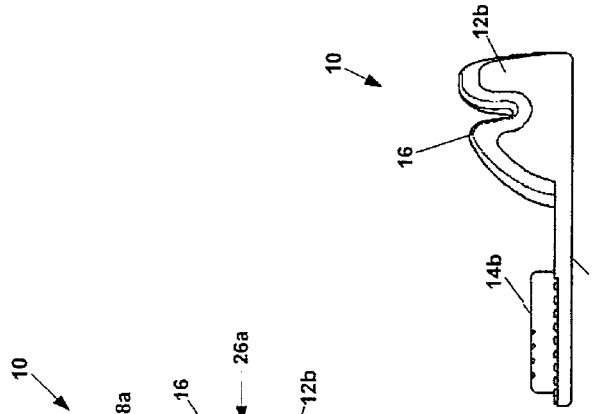
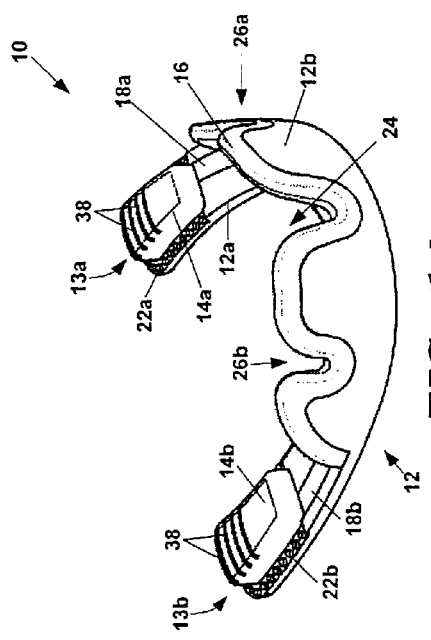
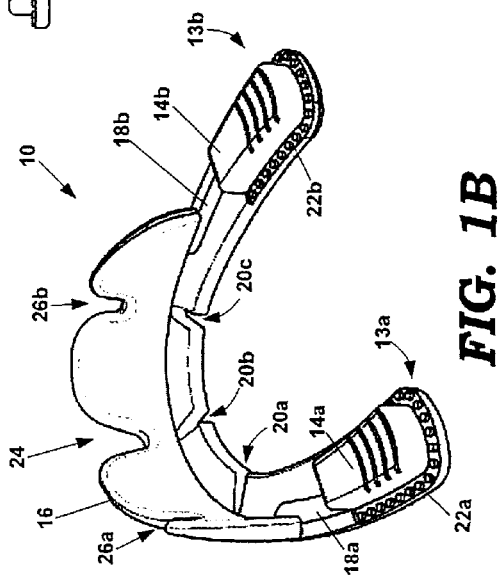

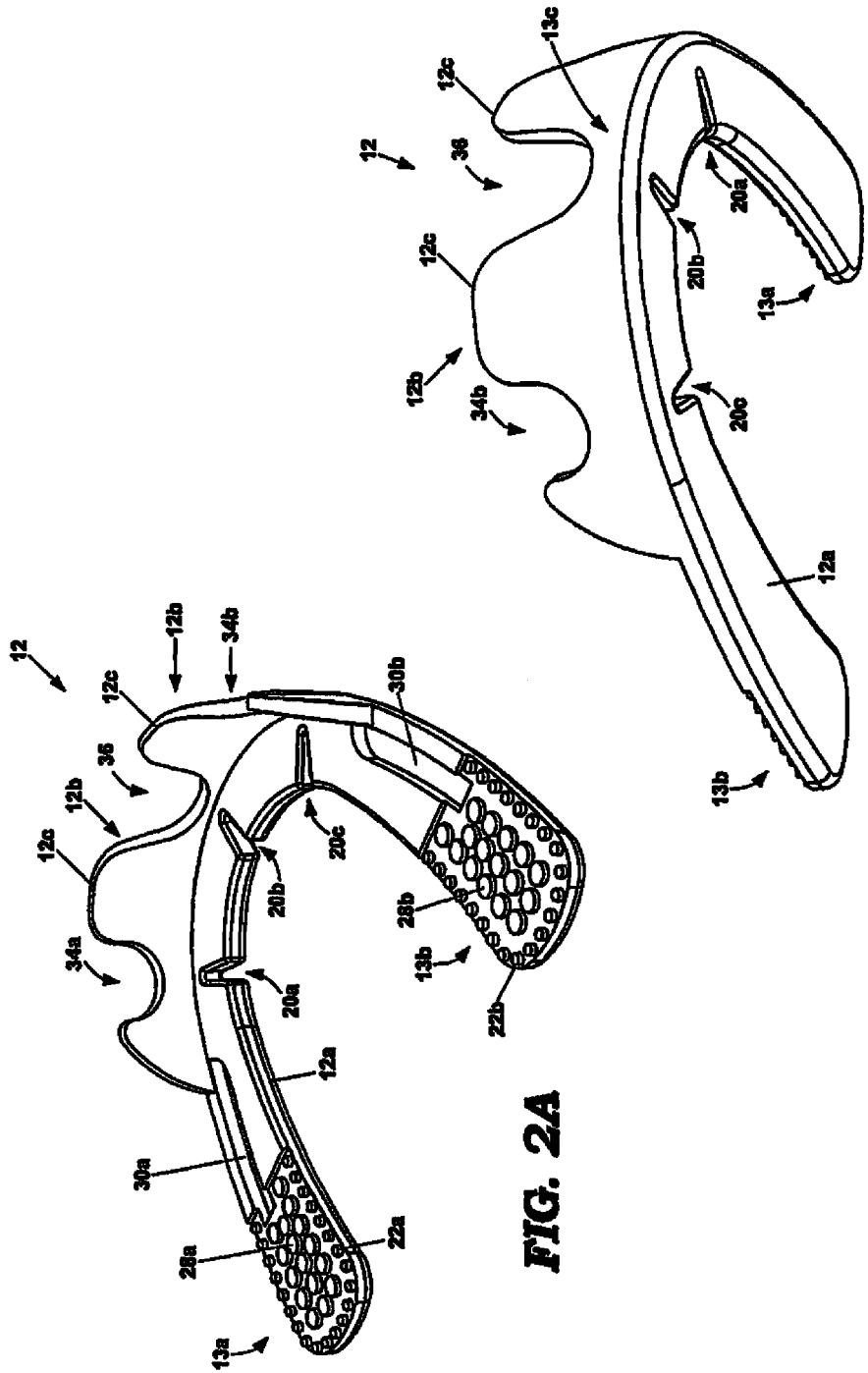

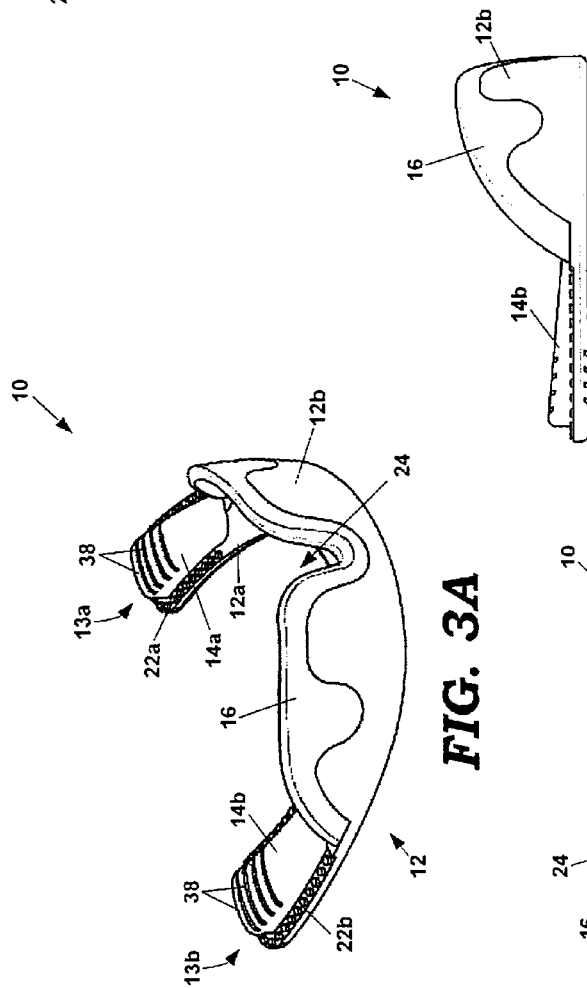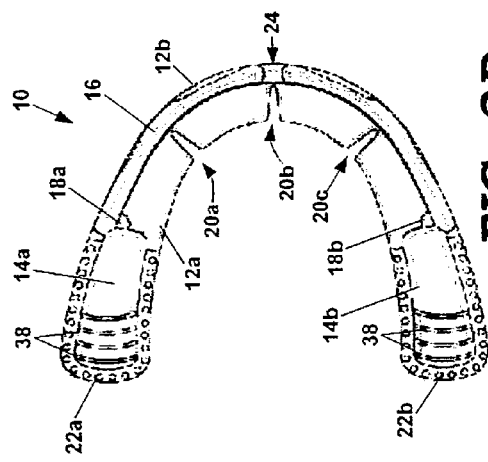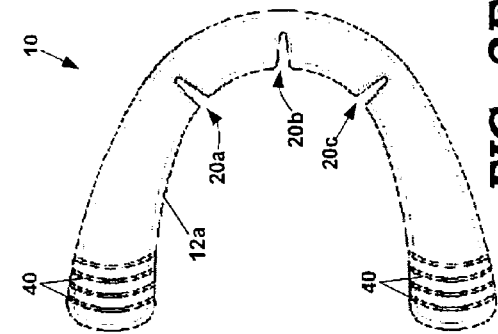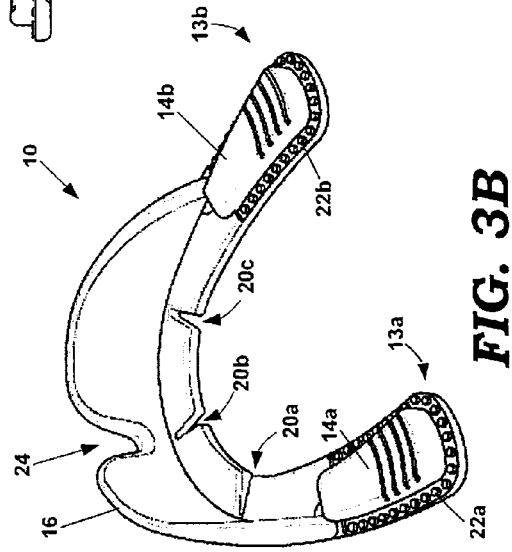

DENTAL GUARD

This application claims priority as a continuation-in-part of U.S. patent application Ser. No. 11/608,274 filed Dec. 8, 2006, titled DENTAL GUARD.

FIELD

This invention relates to the field of dental appliances. More particularly, this invention relates to a dental guard for prevention of the grinding of teeth associated with Bruxism.

BACKGROUND

Bruxism is clenching and/or grinding of the teeth caused by the activation of a reflex chewing activity. Bruxism can cause chips and cracks in the teeth and wear of the biting surface. Bruxism typically occurs during sleep. In a typical case, the canines and incisors move laterally against each other, thereby causing abrasion of tooth enamel removal of the sharp biting surfaces and flattening of the edges of the teeth. Sometimes there is a tendency to grind the molars together, which can be loud enough to wake a sleeping partner. In some cases, clenching occurs without significant lateral jaw movement.

Although dental guards exist for preventing Bruxism, prior guards have not provided a comfortable fit in the wearer's mouth. Due to discomfort associated with prior guards, many Bruxism sufferers have given up on the use of guards to treat the problem during sleep.

What is needed is a custom-fitted dental guard to prevent Bruxism that is comfortable enough to be worn overnight by persons of various mouth sizes and mouth geometry while maintaining comfort, retention and full occlusions.

SUMMARY

The above and other needs are met by a dental appliance for preventing grinding contact between upper and lower teeth of a wearer. In preferred embodiments, the appliance includes a base member having a generally U-shaped horizontal portion and a substantially vertical portion. The U-shaped portion includes opposing first and second posterior sections for positioning between upper and lower molars of the wearer, and an anterior section disposed between the first and second posterior sections. The anterior section has an arcuate curvature substantially matching the curvature of the dental arch of most wearers. The vertical portion of the base member, which is connected to a forward edge of the anterior section of the horizontal portion, has an arcuate curvature substantially following the curvature of the anterior section of the horizontal portion. The horizontal portion of the base member preferably includes one or more horizontal notches for accommodating horizontal flexure of the base member.

The appliance includes first and second molar pads that are attached to the upper surfaces of the first and second posterior sections of the base member horizontal portion. The first and second molar pads are formed from a thermoplastic material, such as an ethylene vinyl acetate, having a Vicat softening temperature below that of the base member.

The appliance also includes a substantially vertical anterior flange that is attached to the vertical portion of the base member. In preferred embodiments, the anterior flange has a pair of substantially vertical notches for accommodating the upper canine teeth of the wearer. Like the molar pads, the anterior flange is formed from a thermoplastic material having a Vicat softening temperature below that of the base member for optimal fit and retention.

The appliance further includes one or more anterior occlusal pads attached to an upper surface of the anterior section of the horizontal portion of the base member. The anterior occlusal pads are preferably disposed adjacent the horizontal notches in the horizontal portion of the base member. In preferred embodiments, the anterior occlusal pads are also formed from a thermoplastic material having a Vicat softening temperature below that of the base member.

In some embodiments, the horizontal notches of the base member comprise first, second and third horizontal notches. The anterior occlusal pads of these embodiments comprise a first anterior occlusal pad disposed between the first and second horizontal notches, and a second anterior occlusal pad disposed between the second and third horizontal notches. Some embodiments further comprise a third anterior occlusal pad disposed between the first horizontal notch and the first molar pad, and a fourth anterior occlusal pad disposed between the third horizontal notch and the second molar pad. In some embodiments, the third occlusal pad and the first molar pad comprise a continuous pad structure, and the fourth occlusal pad and the second molar pad comprise a continuous pad structure.

In some embodiments, the outer surface of each of the first and second molar pads has trim template lines molded therein. These template lines may be used to provide for symmetrical trimming of the molar pads and posterior sections of the base member to achieve a customized fit. Template lines are usable from either above or below.

In preferred embodiments, the posterior sections of the base member include adhesion-enhancement features molded therein. The adhesion-enhancement features may include central features for enhancing adhesion of the molar pads to the base member during an injection over-molding process. The adhesion-enhancement features may also include peripheral features for enhancing adhesion of molar pad material that is extruded during the process of fitting the dental appliance to the wearer.

The base member of the dental appliance is preferably constructed from a material having a Vicat softening temperature of at least about 65° C. and the anterior occlusal pads, molar pads and anterior flange are constructed from a material having a Vicat softening temperature of less than about 46° C.

Preferably, the anterior occlusal pads, the molar pads and anterior flange are attached to the base member by injection over-molding. To accommodate the flow of material during the injection over-molding process, the horizontal portion of the base member includes material-flow channels extending between the vertical portion of the base member and the opposing posterior sections of the base member. These channels allow the over-mold material to flow from the anterior occlusal pads and the anterior flange to the molar pads during the injection molding process.

BRIEF DESCRIPTION OF THE DRAWINGS

Further advantages of the invention are apparent by reference to the detailed description in conjunction with the figures, wherein elements are not to scale so as to more clearly show the details, wherein like reference numbers indicate like elements throughout the several views, and wherein:

FIGS. 1A-1E depict a dental appliance constructed according to a first embodiment of the invention;

FIGS. 2A-2B depict a base member of a dental appliance constructed according to a preferred embodiment of the invention;

FIGS. 3A-3E depict a dental appliance constructed according to a second embodiment of the invention;

DETAILED DESCRIPTION

Figure 4A:
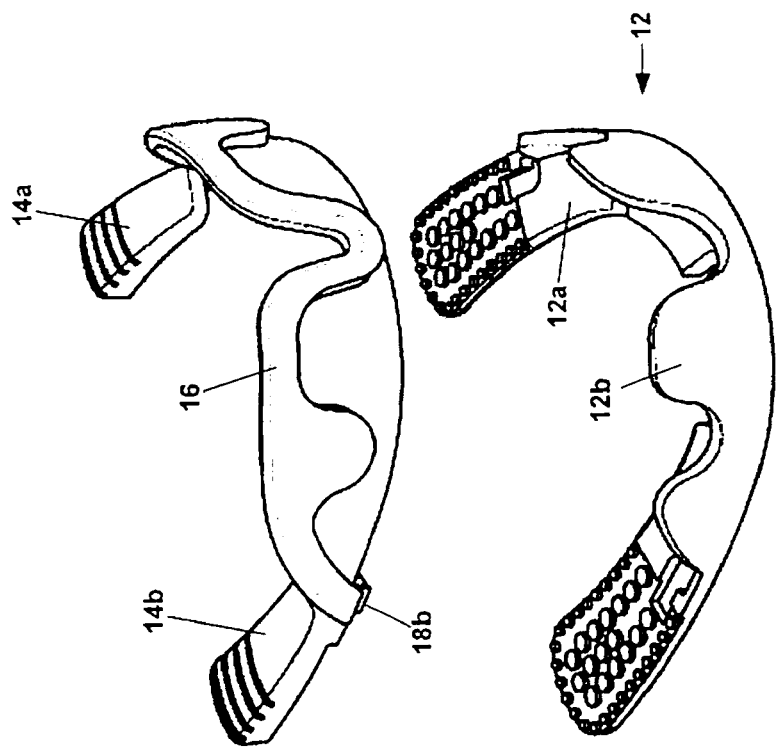
FIGS. 4A and 4B depict exploded views of dental appliances constructed according to first and second embodiments of the invention.
Figure 4B:
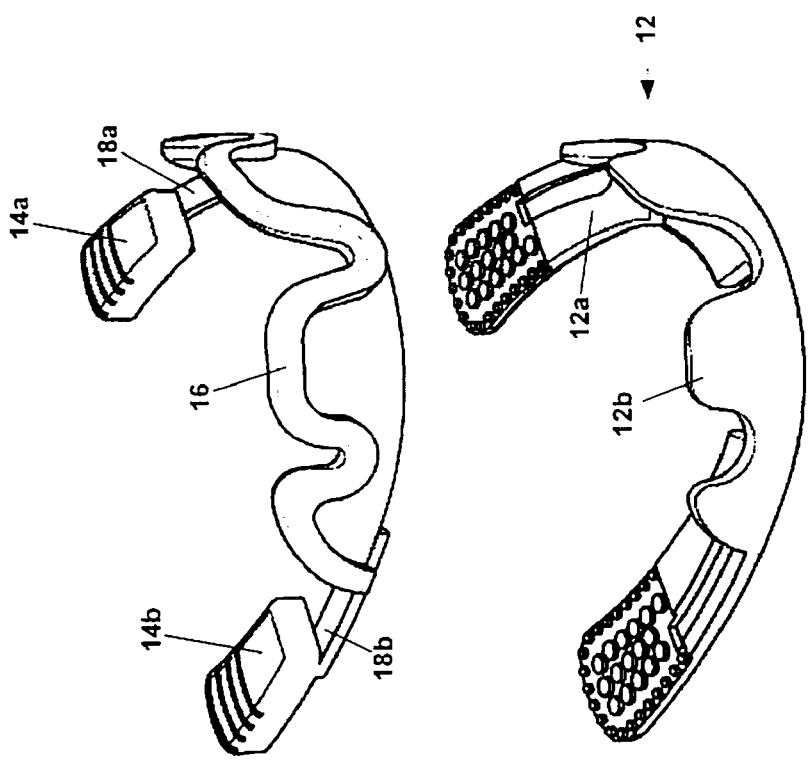

FIGS. 1A-1E, 2A-2B and 4A depict a dental guard appliance 10 constructed in accordance with a first preferred embodiment of the invention. FIGS. 3A-3E, 2A-2B and 4B depict a dental guard appliance 10 constructed in accordance with a second preferred embodiment of the invention. According to both embodiments, the appliance 10 comprises a generally U-shaped base member 12, first and second overmolded molar pads 14a and 14b, and an over-molded anterior flange 16. Preferably, the base member 12 is formed by injection molding a first thermoplastic resin into a base mold cavity. The molded base member 12 is then placed into a second mold cavity into which is injected a second thermoplastic resin that bonds to the base member 12 and forms the over-molded features 14a-14b and 16.

As shown in FIGS. 2A and 2B, the base member 12 of both embodiments comprises a generally flat horizontal portion 12a and a vertical peripheral portion 12b. The horizontal portion 12a includes opposing first and second posterior sections 13a and 13b which, when the appliance 10 is in the wearer's mouth, are positioned between the upper and lower molars. Between the first and second posterior sections 13a-13b is an anterior section 136c having an arcuate curvature that substantially matches the curvature of the dental arch of the wearer. The vertical portion 12b has an uppermost edge 12c.

The base member 12 is preferably injection molded from a thermoplastic material having a Vicat softening temperature of at least about 65° C., which is significantly higher than the temperature to which the appliance 10 is raised during the fitting procedure. In the preferred embodiment, the base member 12 is formed from an ethylene methyl acrylate copolymer, such as Elvaloy® 1209 (70° C. Vicat softening point, 98 Shore A hardness) or Elvaloy® 1609 (70° C. Vicat softening point, 97 Shore A hardness), both of which are manufactured by Dupont™.

In an alternative embodiment, the base member 12 may be formed from a 50-50 blend of Dupont™ Elvax® 750, which is an ethylene vinyl acetate (EVA) copolymer, and Pellethane® 2103-70A, which is a thermoplastic polyurethane elastomer (TPU). In yet another alternative embodiment, the base member 12 may be formed from a non-blended EVA material, such as Dupont™ Elvax® 470 (68° C. Vicat softening temperature, 90 Shore A hardness, 18% vinyl acetate) or Dupont™ Elvax® 650Q (65° C. Vicat softening temperature. 93 Shore A hardness, 12% vinyl acetate). In these alternative embodiments, the hardness of the base member 12 may be decreased by increasing the percentage of TPU, such as Pellethane® 2103-70A (75° C. Vicat softening temperature, 70 Shore A hardness) or Desmopan® KU 2-8670 (70 Shore A hardness). The hardness may be increased by addition of a polyethylene (PE) material.

In the preferred embodiment, the posterior sections 13a-13b of the horizontal portion 12a of the base member 12 include a set of molded central adhesion-enhancement features 28a and 28b that increase the shear adhesion of the over-molded molar pads 14a-14b. These features 28a-28b prevent the molar pads 14a-14b from detaching from the base member 12 when the pads 14a-14b are exposed to shear stresses associated with the grinding lateral movement of molar teeth.

Surrounding the central adhesion-enhancement features 28a-28b are a set of molded peripheral cylindrical features 22a and 22b. During the fitting process, the over-molded molar pads 14a-14b are squeezed between the base member 12 and the downwardly-pressing molars. This causes the softened material of the molar pads 14a-14b to extrude outward beyond the central features 28a-28b and onto the peripheral features 22a-22b. When the molar pads 14a-14b cool after the fitting process, the peripheral features 22a-22b serve to enhance adhesion of the extruded edge portions of the molar pads 14a-14b to the peripheral portions of the base member 12.

With continued reference to FIG. 2A, the upper surface of the horizontal portion 12a of the base member 12 includes a pair of channels 30a and 30b that allow the over-mold thermoplastic material to flow between the anterior flange 16 and the molar-pads 14a-14b during the process of injection molding the over-molded portions.

The horizontal portion 12a of the base member 12 includes horizontal notches 20a, 20b and 20c extending from an inner edge of the horizontal portion 12a to points adjacent the inner surface of the vertical peripheral portion 12b. These notches 20a-20c allow the base member 12 to flex in the horizontal plane without distortion of the horizontal portion 12a, thereby providing a comfortable fit in mouths of various sizes. The horizontal notches 20a, 20b and 20c are also referred to herein as the first, second and third horizontal notches, respectively.

As shown in FIGS. 1A-1E and 4A, one embodiment of the over-molded anterior flange 16 includes several substantially vertical notches 24, 26a and 26b in the upper edge of the flange 16. The notches 26a-26b accommodate the wearer's canine teeth and surrounding gum tissue, and the notch 24 accommodates the connecting tissue that extends between the wearer s upper lip and gum. During the fitting process, the softened over-mold material conforms to the shape of the wearer's mouth in these regions, thereby further enhancing comfort. As shown in FIGS. 2A and 2B, the vertical peripheral portion 12b of the base member 12 includes notches 34a, 34b and 36 to accommodate the over-mold material that forms the notches 26a, 26b and 24, respectively.

The over-molded portions of the dental appliance 10, including the molar pads 14a-14b and the anterior flange 16, are preferably injection molded from a thermoplastic material having a Vicat softening temperature of less than about 46° C., which is lower than the temperature to which the appliance 10 is raised during the fitting procedure. Although the invention is not limited to any particular formulation of the over-molded portions, the over-molded portions of preferred embodiments are formed from a material comprising at least about 35% vinyl acetate (by weight). For example, the overmolded portions may be formed from one or more of the following ethylene vinyl acetate (EVA) materials: DuPont™ Elvax® 150 (36° C. Vicat softening point, 73 Shore A hardness. 32% vinyl acetate): Ateva® 3325AC (68 Shore A hardness, 33% vinyl acetate); Ateva® 2604A (46° C. Vicat softening point, 84 Shore A hardness. 26% vinyl acetate); and Elvax® 240 (40° C. Vicat softening point, 78 Shore A hardness, 28% vinyl acetate). In one preferred embodiment, the over-molded portions are formed from a resin comprising a mixture of two ethylene vinyl acetate (EVA) copolymers: AT Plastics Aetva® (40% vinyl acetate) and Elvax® 150 (33% vinyl acetate).

In the embodiment of the invention depicted in FIGS. 3A-3E and 4B, the base member 12 is preferably identical to the base member 12 of the embodiment depicted in FIGS. 1A-1D and 4A. However, the molar pads 14a-b and the anterior flange 16 of the embodiment of FIGS. 3A-3E and 4B are different in several respects. First, the molar pads 14a-b are longer, such that the front edges of the molar pads 14a-b reach to a point adjacent or touching the rear edges of the anterior flange 16. Second, the upper surface of the molar pads 14a-b are angled with respect to the upper surface of the horizontal portion 12a of the base member 12. The angle of the upper surface of the molar pads 14a-b is designed to provide more over-mold material toward the rear of the molar pads 14a-b. This accommodates the larger surface area of the molars and the greater pressure exerted by the molars on the molar pads 14a-b. Third, the anterior flange 16 of this embodiment is not notched in the area of the upper canines. Even without canine notches, the softened over-mold material of the anterior flange 16 conforms itself to the shape of the wearer's teeth and gums in the region surrounding the upper canines during the fitting process.

To customize the fit of the dental guard appliance 10, the wearer may adjust the overall length by trimming away portions of the rear edges of the posterior portions 13a-13b of the base member 12 and the molar pads 14a-14b. To accommodate the trimming operation, the molar pads 14a-14b of a preferred embodiment include a series of impressions that serve as trim template lines 38. By trimming along corresponding lines 38 on either side the wearer can be assured of achieving a symmetrical fit. As shown in FIG. 3E, the lower surface of the horizontal portion 12a of the base member 12 may also include trim template lines 40 to assist in the trimming process.

To determine how much of the posterior portions 13a-b should be trimmed away, the wearer positions the appliance 10 in the wearer's mouth and closes down the teeth on the appliance 10. If the arch (U-shape) of the appliance 10 is too wide or too narrow the wearer may stretch or squeeze the guard to match the shape of the wearer's mouth. The optimal fit is when all of the wearer's teeth are sitting on the appliance 10 comfortably. If the posterior portions 13a-b of the appliance 10 extend beyond the wearer's rear-most molars and cause discomfort, the wearer can trim them along the trim lines 38. At first, the wearer should trim at the first line 38 from the rear and check the fit of the appliance 10 again. If it is still is not comfortable, the wearer may trim at the second trim line 38, keeping in mind that all teeth should be in contact with the appliance 10. This process can be continued until the appliance 10 feels comfortable and all teeth are cushioned by the appliance 10.

To custom fit the appliance 10 to the teeth and gums of the wearer, the appliance 10 is first immersed in boiling water for about 60 seconds so that the thermoplastic material of the molar pads 14a-14b and anterior flange 16 reaches a temperature that is above its softening temperature. To bring the temperature of the appliance to a point that can be comfortably withstood by the oral tissue of the wearer, the appliance 10 should be dipped in a container of cool water for about one second. The appliance 10 is then inserted into and symmetrically aligned within the oral cavity so that all of the wearer's teeth are in contact with the appliance 10. The wearer next applies firm pressure to seat the upper molars on the molar pads 14a-14b, and then applies biting pressure to imbed the molars into the molar pads 14a-14b. The biting pressure causes little, if any, deformation of the material of the base member 12 because the softening temperature of the base material is not reached during the heating step. Using his/her fingers, the wearer should press in along the gum line on both sides of the appliance 10 from the front to the rear using equal amounts of pressure. This forms the softened over-mold material of the molar pads 14a-b and the flange up and around the wearer's teeth. The wearer may also suck in to remove excess moisture and create a suction that allows the appliance 10 to stay in place comfortably. Once the wearer feels that a comfortable fit has been achieved, the appliance 10 should be placed in a container of cold water for about 30 seconds to "set" the over-mold material. Upon cooling, the material of the molar pads 14a-14b retains the impression of the upper molars, and the anterior flange 16 retains the shape of the gums and inner oral tissue of the wearer's upper lip. The result is a custom-fitted reusable dental appliance that may be comfortably worn during sleep to prevent Bruxism.

Figure 5A:
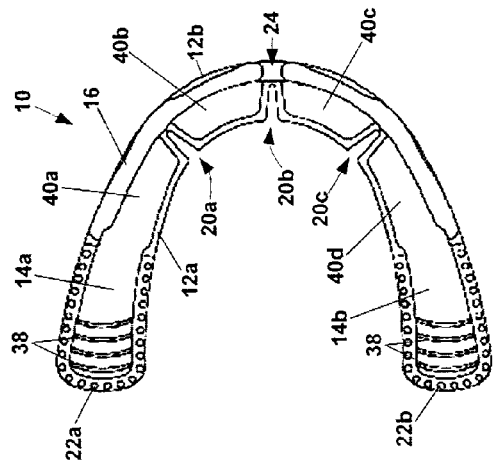
FIGS. 5A-5E depict a dental appliance constructed according to a third embodiment of the invention.
Figure 5B:
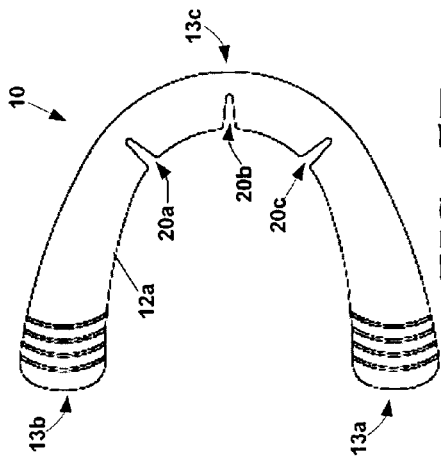
Figure 5C:
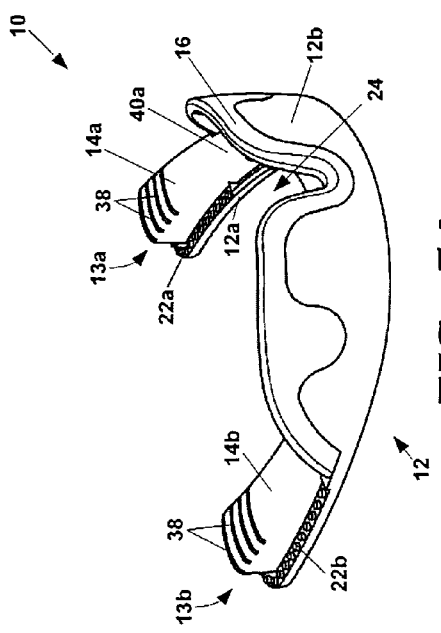
Figure 5D:
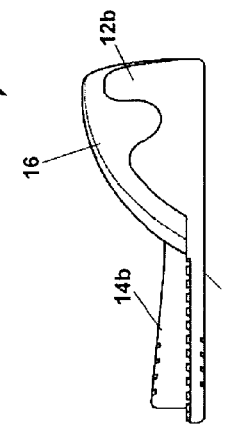
Figure 5E:
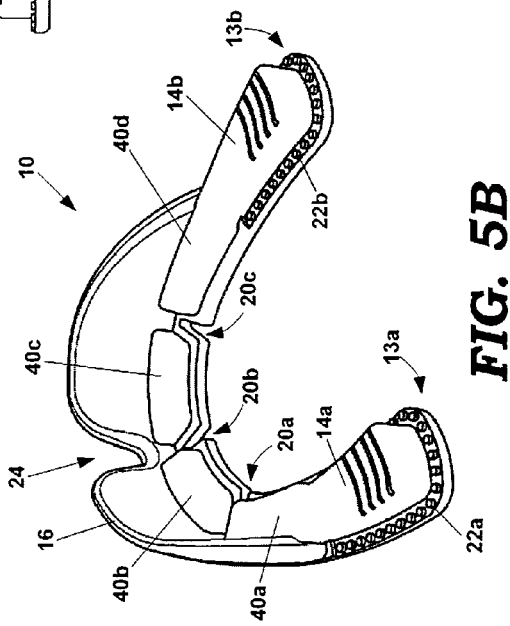

An alternative embodiment of the invention is depicted in FIGS. 5A-5E. This embodiment is similar to the embodiment of FIGS. 3A-3E except that in the embodiment of FIGS. 5A-5E the appliance 10 includes anterior occlusal pads 40a, 40b, 40c and 40d attached to the upper surface of the base member 12 and formed integrally with the anterior flange 16. The anterior occlusal pads 40b, 40c, 40a and 40d are also referred to herein as the first, second, third and fourth anterior occlusal pads, respectively. The anterior occlusal pads 40a-40d are preferably formed from the same heat-formable over-mold material and in the same molding step as the molar pads 14a-14b and the anterior flange 16. When the appliance is fitted as described above, the wearer's upper front teeth are embedded in the softened anterior occlusal pads 40a-40d. This enhances the custom fit of the appliance 10, thereby providing further comfort for the wearer.

As shown in FIGS. 5A-5E, the two middle anterior occlusal pads 40b and 40c are disposed to either side of the central horizontal notch 20b, with pad 40b disposed between notches 20a and 20b and pad 40c disposed between notches 20b and 20c. In the preferred embodiment, anterior occlusal pad 40a is formed integrally with molar pad 14a and anterior occlusal pad 40c is formed integrally with molar pad 14b.

In some preferred embodiments, the base member 12 is formed of a translucent material of a first color, and the anterior occlusal pads, the molar pads and the anterior flange are formed of a translucent material of a second color that is different from the first color. In one embodiment, the first color is a translucent gray and the second color is a translucent blue.

The foregoing description of preferred embodiments for this invention have been presented for purposes of illustration and description. They are not intended to be exhaustive or to limit the invention to the precise form disclosed. Obvious modifications or variations are possible in light of the above teachings. The embodiments are chosen and described in an effort to provide the best illustrations of the principles of the invention and its practical application, and to thereby enable one of ordinary skill in the art to utilize the invention in various embodiments and with various modifications as are suited to the particular use contemplated. All such modifications and variations are within the scope of the invention as determined by the appended claims when interpreted in accordance with the breadth to which they are fairly, legally, and equitably entitled.

What is claimed is:

1. A dental appliance for preventing grinding contact between upper and lower teeth of a wearer, the appliance comprising:

a base member having a Vicat softening temperature that is higher than the temperature to which the appliance is raised during the fitting process comprising:
  a generally U-shaped horizontal portion having:
    opposing first and second posterior sections for positioning between upper and lower molars of the wearer, the first and second posterior sections each comprising a peripheral portion having a set of peripheral features therein and central adhesion-enhancement features having a Vicat softening temperature higher than the temperature to which the appliance is raised during the fitting process;
    an anterior section disposed between the first and second posterior sections, the anterior section having an arcuate curvature substantially matching the curvature of the dental arch of the wearer; and
    one or more notches for accommodating horizontal flexure of the base member; and
  a substantially vertical portion connected to a forward edge of the anterior section of the horizontal portion, the vertical portion having an arcuate curvature substantially following the curvature of the anterior section of the horizontal portion;
one or more anterior occlusal pads attached to an upper surface of the anterior section of the horizontal portion of the base member, the one or more anterior occlusal pads disposed adjacent the one or more notches in the horizontal portion of the base member and formed from a thermoplastic material having a Vicat softening temperature below that of the base member;
first and second molar pads, each attached to an upper surface of a corresponding one of the first and second posterior sections of the horizontal portion of the base member and surrounded by the peripheral portions of the first and second posterior sections, the first and second molar pads formed from a thermoplastic material having a Vicat softening temperature below that of the base member; and
a substantially vertical anterior flange attached to the vertical portion of the base member, the anterior flange formed from a thermoplastic material having a Vicat softening temperature below that of the base member.

2. The dental appliance of claim 1 wherein the one or more anterior occlusal pads further comprise a third anterior occlusal pad disposed between the first notch and the first molar pad, and a fourth anterior occlusal pad disposed between the third notch and the second molar pad.

3. The dental appliance of claim 2 wherein the third occlusal pad and the first molar pad comprise a continuous pad structure, and the fourth occlusal pad and the second molar pad comprise a continuous pad structure.

4. The dental appliance of claim 1 wherein:
the one or more notches of the base member comprise first, second and third notches; and
the one or more anterior occlusal pads comprise a first anterior occlusal pad disposed between the first and second notches and a second anterior occlusal paid disposed between the second and third notches.

5. The dental appliance of claim 1 wherein an outer surface of each of the first and second molar pads has trim template lines molded therein.

6. The dental appliance of claim 1 wherein the central adhesion-enhancement features include central features for enhancing adhesion of the molar pads to the base member during an injection over-molding process.

7. The dental appliance of claim 1 wherein the base member is constructed from a material having a Vicat softening temperature of at least about 65° C.

8. The dental appliance of claim 1 wherein the one or more anterior occlusal pads, the first and second molar pads and the anterior flange are constructed from a material having a Vicat softening temperature of less than about 46° C.

9. The dental appliance of claim 1 wherein the one or more anterior occlusal pads, the first and second molar pads and the anterior flange are attached to the base member of injection over-molding.

10. The dental appliance of claim 1 wherein the one or more anterior occlusal pads, the first and second molar pads and the anterior flange form a continuous over-molded structure.

11. The dental appliance of claim 1 wherein an upper surface of each of the first and second molar pads is disposed at an angle relative to the horizontal portion of the base member.

12. The dental appliance of claim 1 wherein the base number is formed of a translucent material of a first color, and the one or more anterior occlusal pads, the molar pads and the anterior flange are formed of a translucent material of a second color that is different from the first color.

13. The dental appliance of claim 1 wherein the peripheral features are configured to enhance adhesion of the first and second molar pads extruded over the peripheral portion during a process of fitting the dental appliance to the wearer.

14. A dental appliance for preventing grinding contact between upper and lower teeth of a wearer, the appliance comprising:
  a base member comprised of first and second horizontal posterior sections each having peripheral portions with central adhesion-enhancement features molded into the first and second horizontal posterior sections within the peripheral portion, the base member and the central adhesion-enhancement features formed from a first resin having a Vicat softening temperature of at least about 65° C.; and
  an anterior occlusal pad structure, molar pads and an anterior flange over-molded on the base member, the anterior occlusal pad structure, the molar pads and the anterior flange formed from a second resin comprising an ethylene vinyl acetate copolymer having about 35% by weight vinyl acetate, the molar pads being surrounded by the peripheral portions of the first and second horizontal posterior sections.

15. The dental appliance of claim 14 wherein the first resin is translucent and has a first color, and second resin is translucent and has a second color that is different from the first color.

16. A U-shaped dental appliance, the appliance comprising:
  opposing first and second horizontal posterior sections for positioning between upper and lower molars of the wearer, an upper surface of the posterior sections having a Vicat softening temperature that is higher than the temperature to which the appliance is raised during the fitting process and comprising peripheral portions with peripheral features molded into the upper surface of the first and second posterior sections and central adhesion-enhancement features having a Vicat softening temperature higher than the temperature to which the appliance is raised during the fitting process molded into the upper surface of the first and second posterior sections;
  first and second molar pads, each attached to the upper surface of a corresponding one of the first and second posterior sections of the horizontal portion of the base member and surrounded by the peripheral portions of the first and second posterior sections; and an anterior section disposed between the first and second posterior sections, the anterior portion comprising:

a horizontal portion having one or more notches for accommodating horizontal flexure of the base member;

a substantially vertical portion connected to a forward edge of the horizontal portion;

a substantially vertical flange bonded to the vertical portion having a softening temperature below that of the substantially vertical portion; and one or more anterior occlusal pads attached to an upper surface of the anterior horizontal portion, the one or more anterior occlusal pads disposed adjacent the one or more notches in the horizontal anterior portion and having a softening temperature below that of the base member.

17. The dental appliance of claim 16 wherein the molar pads are bonded to the upper surface within the peripheral portions and configured such that during fitting, extruded portions of the molar pads extend outward beyond the central features and onto the peripheral features.

18. The dental appliance of claim 16 wherein the central adhesion-enhancement features are non-deformable.

* * * * *